United States Patent
Hirokawa et al.

(10) Patent No.: US 10,131,615 B2
(45) Date of Patent: Nov. 20, 2018

(54) MOLDED CATALYST FOR USE IN MANUFACTURE OF METHYL METHACRYLATE, AND METHOD FOR MANUFACTURE OF METHYL METHACRYLATE USING SAME

(71) Applicant: MITSUBISHI GAS CHEMICAL COMPANY, INC., Tokyo (JP)

(72) Inventors: Saori Hirokawa, Niigata (JP); Katsumi Higuchi, Tokyo (JP); Yuuichi Sugano, Niigata (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 15/124,492

(22) PCT Filed: Apr. 8, 2015

(86) PCT No.: PCT/JP2015/060912
§ 371 (c)(1),
(2) Date: Sep. 8, 2016

(87) PCT Pub. No.: WO2015/156301
PCT Pub. Date: Oct. 15, 2015

(65) Prior Publication Data
US 2017/0015615 A1 Jan. 19, 2017

(30) Foreign Application Priority Data
Apr. 10, 2014 (JP) .................................. 2014-080943

(51) Int. Cl.
| | | |
|---|---|---|
| *B01J 29/06* | (2006.01) | |
| *C07C 67/327* | (2006.01) | |
| *B01J 21/16* | (2006.01) | |
| *B01J 29/08* | (2006.01) | |

(52) U.S. Cl.
CPC ............. *C07C 67/327* (2013.01); *B01J 21/16* (2013.01); *B01J 29/08* (2013.01)

(58) Field of Classification Search
CPC .......... B01J 29/08; B01J 21/16; C07C 67/327

USPC ...... 502/63, 64, 68, 69, 72, 79, 80; 560/212, 560/214, 215, 218
See application file for complete search history.

(56) References Cited

U.S. PATENT DOCUMENTS

| | | | |
|---|---|---|---|
| 4,007,134 A | 2/1977 | Liepa et al. | |
| 5,068,399 A | 11/1991 | Naito et al. | |
| 5,250,729 A | 10/1993 | Abe et al. | |
| 5,371,273 A | 12/1994 | Shima et al. | |
| 5,739,379 A | 4/1998 | Shima et al. | |
| 9,630,904 B2 * | 4/2017 | Higuchi ................ | B01J 29/08 |
| 2013/0079553 A1 | 3/2013 | Weiner et al. | |

FOREIGN PATENT DOCUMENTS

| | | |
|---|---|---|
| JP | 50-151795 | 12/1975 |
| JP | 61-501080 | 5/1986 |
| JP | 2-196753 | 8/1990 |
| JP | 3-167155 | 7/1991 |
| JP | 3-167156 | 7/1991 |
| JP | 3-167157 | 7/1991 |
| JP | 6-157413 | 6/1994 |
| JP | 8-188555 | 7/1996 |
| TW | 200702053 A | 1/2007 |
| TW | 201318698 A1 | 5/2013 |
| WO | 85/03240 | 8/1985 |

OTHER PUBLICATIONS

International Search Report issued in Patent Application No. PCT/JP2015/060912, dated Jun. 2, 2015.

* cited by examiner

*Primary Examiner* — Elizabeth D Wood
(74) *Attorney, Agent, or Firm* — Greenblum & Bernstein, P.L.C.

(57) ABSTRACT

The present invention provides a molded catalyst for use in the manufacture of methyl methacrylate, for manufacturing methyl methacrylate from a starting material of methyl α-hydroxyisobutyrate by a vapor phase contact reaction, wherein the molded catalyst for use in the manufacture of methyl methacrylate is characterized in that the molded catalyst includes a synthetic faujasite type zeolite, a lamellar aluminum silicate compound, and a synthetic lamellar magnesium silicate compound, the weight ratio of the lamellar aluminum silicate compound and the synthetic lamellar magnesium silicate compound being 1:5 to 6:1.

9 Claims, No Drawings

MOLDED CATALYST FOR USE IN MANUFACTURE OF METHYL METHACRYLATE, AND METHOD FOR MANUFACTURE OF METHYL METHACRYLATE USING SAME

TECHNICAL FIELD

The present invention relates to a method for producing methyl methacrylate by means of a vapor phase contact reaction using methyl α-hydroxyisobutyrate as a raw material and a molded catalyst for use in the production of methyl methacrylate to be used in the method. Methyl methacrylate has industrially important uses such as a raw material of polymethyl methacrylate, which is excellent in weather resistance and transparency, and a raw material of various methacrylic acid esters.

BACKGROUND ART

The method for producing methyl methacrylate by means of a vapor phase contact reaction using methyl α-hydroxyisobutyrate as a raw material is publicly known. For example, Patent Document 1 discloses a method for producing an α,β-unsaturated carboxylic acid ester in which α-hydroxycarboxylic acid ester, α-alkoxycarboxylic acid ester and β-alkoxycarboxylic acid ester are used solely or in combination as a raw material to carry out a dehydration or dealcoholization reaction with a crystalline alumino silicate as a catalyst. Regarding the crystalline alumino silicate to be used in the production method, the document describes that X-type or Y-type zeolite exhibits particularly excellent catalytic activity. Further, Patent Documents 2, 3 and 4 disclose that a crystalline alumino silicate modified with an alkali metal and/or a platinum group element, in particular, X-type or Y-type zeolite is effective as a catalyst for the production method.

In the case of producing methyl methacrylate from methyl α-hydroxyisobutyrate by means of a vapor phase contact reaction using such a crystalline alumino silicate as a catalyst, it is known that there are problems such as temporal deterioration of the catalyst, which is caused because a high boiling point byproduct covers pore inlets of the crystalline alumino silicate, and coloring of a reaction solution due to by-produced diacetyl.

Regarding these problems, Patent Document 5 discloses that when a transition-type synthetic faujasite-type zeolite having a lattice constant in the boundary region between X type and Y type with the Na content being defined is used, the production of diacetyl that is a coloring substance can be suppressed, and at the same time, the by-production of the high boiling point byproduct can be reduced to maintain the catalytic activity for a long period of time. In this regard, the document describes that a clay having an Al content of less than 5% by weight, in particular, a silica magnesia-based clay is preferably used as a binder for suppressing the by-production of diacetyl.

In addition, Patent Document 6 discloses that when using a catalyst containing, as an active component, a synthetic faujasite-type zeolite with the amount of free alkali being adjusted to 0.1 milliequivalent/g or less, or a molded catalyst obtained by using a clay whose pH is less than 9 when dispersed in water and a synthetic faujasite-type zeolite, the by-production of a high boiling point byproduct that causes temporal deterioration of the catalyst is suppressed, and the catalyst life becomes longer.

PRIOR ART DOCUMENTS

Patent Documents

Patent Document 1: Japanese Laid-Open Patent Publication No. H02-196753
Patent Document 2: Japanese Laid-Open Patent Publication No. H03-167155
Patent Document 3: Japanese Laid-Open Patent Publication No. H03-167156
Patent Document 4: Japanese Laid-Open Patent Publication No. H03-167157
Patent Document 5: Japanese Laid-Open Patent Publication No. H06-157413
Patent Document 6: Japanese Laid-Open Patent Publication No. H08-188555

SUMMARY OF THE INVENTION

Problems to be Solved by the Invention

In the aforementioned Patent Document 5 and Patent Document 6, when producing methyl methacrylate by means of a vapor phase contact reaction using methyl α-hydroxyisobutyrate as a raw material, in order to suppress hydrolysis of the ester group, methanol is supplied to a reactor with the amount thereof being 0.1 to 3.0 times by weight of methyl α-hydroxyisobutyrate to carry out the vapor phase contact reaction. In this regard, not only a dehydration reaction of the hydroxyl group of methyl α-hydroxyisobutyrate, but also a dehydration reaction of methanol occurs, causing by-production of dimethyl ether (hereinafter referred to as DME). Industrially, methanol is recovered in the purification process and reused, but when DME is by-produced, there are drawbacks that the methanol recovery rate in the purification process is decreased, and that the production cost of methyl methacrylate is increased.

Specifically, the problem to be solved by the present invention is to provide a molded catalyst for use in the production of methyl methacrylate, which has a higher methanol recovery rate and a longer catalyst life compared to those of conventional methods, to be used in a method for producing methyl methacrylate by means of a vapor phase contact reaction using methyl αhydroxyisobutyrate as a raw material, and a method for producing methyl methacrylate using the molded catalyst for use in the production of methyl methacrylate.

Means for Solving the Problems

The present inventors diligently made researches on the aforementioned problem, and found that, by using a molded catalyst, which is obtained by molding a synthetic faujasite-type zeolite and a binder component obtained by mixing a lamellar aluminum silicate compound and a synthetic lamellar magnesium silicate compound at a specific ratio, as a catalyst for use in the production of methyl methacrylate, the amount of by-produced DME is more reduced and a higher methanol recovery rate is maintained while a longer catalyst life is provided compared to conventional methods, and thus the present invention was achieved.

Specifically, the present invention is as follows:
<1> A molded catalyst for use in the production of methyl methacrylate, for producing methyl methacrylate from methyl α-hydroxyisobutyrate as a raw material by means of a vapor phase contact reaction, wherein the molded catalyst comprises a synthetic faujasite-type zeolite, a lamellar aluminum silicate compound and a synthetic lamellar magnesium silicate compound, the weight ratio between the lamellar aluminum silicate compound and the synthetic lamellar magnesium silicate compound being 1:5 to 6:1.

<2> The molded catalyst for use in the production of methyl methacrylate according to item <1>, wherein an aqueous dispersion containing 2% by weight of a component of the molded catalyst has a pH value of 10.2 to 10.8.

<3> The molded catalyst for use in the production of methyl methacrylate according to item <1> or <2>, wherein the amount of free sodium in the molded catalyst is 0.03 milliequivalent/g or less.

<4> The molded catalyst for use in the production of methyl methacrylate according to any one of items <1> to <3>, wherein the ratio of the total amount of the lamellar aluminum silicate compound and the synthetic lamellar magnesium silicate compound to the total amount of the synthetic faujasite-type zeolite, the lamellar aluminum silicate compound and the synthetic lamellar magnesium silicate compound is 3 to 30% by weight.

<5> The molded catalyst for use in the production of methyl methacrylate according to any one of items <1> to <4>, wherein the lamellar aluminum silicate compound is a clay compound mainly composed of at least one substance selected from montmorillonite, beidellite and kaolinite.

<6> The molded catalyst for use in the production of methyl methacrylate according to any one of items <1> to <5>, wherein the lamellar aluminum silicate compound is a clay compound mainly composed of montmorillonite.

<7> The molded catalyst for use in the production of methyl methacrylate according to any one of items <1> to <6>, wherein the synthetic lamellar magnesium silicate compound is a synthetic hectorite.

<8> A method for producing methyl methacrylate, wherein methyl methacrylate is produced by means of a vapor phase contact reaction using methyl α-hydroxyisobutyrate as a raw material in the presence of the molded catalyst for use in the production of methyl methacrylate according to any one of items <1> to <7>.

<9> The method for producing methyl methacrylate according to item <8>, wherein methanol is used as a diluent in an amount of 0.1 to 3.0 times by weight of methyl α-hydroxyisobutyrate.

Advantageous Effect of the Invention

According to the present invention, it is possible to provide a molded catalyst, which has a higher methanol recovery rate and a longer catalyst life compared to those of conventional methods, to be used in a method for producing methyl methacrylate by means of a vapor phase contact reaction using methyl α-hydroxyisobutyrate as a raw material, and a method for producing methyl methacrylate using the molded catalyst.

EMBODIMENTS FOR CARRYING OUT THE INVENTION

The molded catalyst for use in the production of methyl methacrylate of the present invention is obtained by molding a synthetic faujasite-type zeolite, a lamellar aluminum silicate compound and a synthetic lamellar magnesium silicate compound.

Firstly, the synthetic faujasite-type zeolite will be explained. The synthetic faujasite-type zeolite that can be used in the present invention is an alumino silicate having a FAU-type crystal structure, "FAU" being a three-letter code representing a crystal structure of a crystalline molecular sieve defined by the International Zeolite Association (IZA). Regarding the type of the synthetic faujasite-type zeolite, generally known are the X type and the Y type, which have the same crystal structure but have a different chemical composition, i.e., a different atomic ratio of Si/Al. Both the types can be suitably used. Among them, the transition type described in E. Dempsey, G. H. Kuhl, D. H. Olson, J. Phys. Chem., 73, 387 (1969) can be particularly suitably used. According to the document, a transition-type synthetic faujasite-type zeolite means a zeolite having a lattice constant, which is measured by X-ray diffraction, of 24.80 to 24.94 Å.

The cation type of the synthetic faujasite-type zeolite to be used in the present invention is not particularly limited, but the sodium ion type is preferred, and it is particularly preferred that the atomic ratio of Na to Al in zeolite (Na/Al atomic ratio) is 0.90 to 1.02. Further, the synthetic faujasite-type zeolite is generally produced by filtering, washing and drying a crystal obtained by hydrothermal synthesis under alkaline conditions. In this process, when washing is insufficient, an alkaline component remains in the crystal, and a zeolite in which the amount of free alkali is large as defined below is obtained. The amount of free alkali is a numerical value which is measured and calculated by titration of 4 wt % aqueous dispersion of zeolite with 0.01N hydrochloric acid.

The amount of free alkali in the synthetic faujasite-type zeolite to be used in the present invention is preferably 0.1 milliequivalent or less per 1 g of zeolite.

Next, the binder to be used at the time of forming a molded body will be explained. The synthetic faujasite-type zeolite is produced in the form of fine powder unless it is produced as a molded binderless zeolite. In the case of industrial use as a fixed bed catalyst, it is difficult to use zeolite in the form of fine powder directly. For this reason, it is generally used in the form of a molded body having an appropriate shape such as a spherical shape and a column shape. However, since zeolite fine powder itself does not have mutual bonding capability, a binder is used for imparting appropriate plasticity and strength thereto. The molded catalyst of the present invention contains, as binder components, the lamellar aluminum silicate compound and the lamellar magnesium silicate compound at a specific ratio.

The reason thereof is as described below. The methanol recovery rate and the catalyst life in a reaction of synthesizing methyl methacrylate by means of a dehydration reaction of methyl α-hydroxyisobutyrate are good when the amount of sodium ion in the synthetic faujasite-type zeolite that is an active component of the reaction is appropriately adjusted. In this regard, by using a mixture of the lamellar aluminum silicate compound and the synthetic lamellar magnesium silicate compound as a binder, the amount of sodium ion in the synthetic faujasite-type zeolite can be suitably adjusted in the form of the molded catalyst.

The present inventors examined behavior of the amount of by-produced DME and the catalyst life in the reaction of synthesizing methyl methacrylate by means of a dehydration reaction of methyl α-hydroxyisobutyrate in detail, and found: the larger the amount of sodium ion in the synthetic faujasite-type zeolite that is an active component of the reaction is, the smaller the amount of by-produced DME is; the larger the amount of sodium ion is, the shorter the catalyst life is; but none of these has a simple linear relationship; and both the amount of by-produced DME and the catalyst life are good in the intermediate region.

However, since synthetic faujasite-type zeolite powder alone does not have moldability as described above, in the case of the molded catalyst, it is required to include not only zeolite, but also a binder component for appropriately controlling the amount of sodium ion. In this regard, the present inventors also examined behavior of a solution obtained by dispersing a binder component in water in detail. It was found that the lamellar aluminum silicate compound such as bentonite is predisposed to adsorb sodium ion in an aqueous solution, and that the synthetic lamellar magnesium silicate compound such as a synthetic hectorite is predisposed to supply sodium ion to an aqueous solution. Moreover, when mixing the lamellar aluminum silicate compound and the synthetic lamellar magnesium silicate compound at a specific ratio to be used as a binder, the amount of sodium ion in the synthetic faujasite-type zeolite can be appropriately adjusted even in the form of the molded catalyst, and it is possible to obtain a catalyst having a high methanol recovery rate and a long catalyst life, wherein the amount of by-produced DME is reduced.

Meanwhile, in the case of a molded catalyst using only the lamellar aluminum silicate compound, the amount of by-produced DME is larger because the amount of sodium ion in the synthetic faujasite-type zeolite tends to be smaller. Conversely, in the case of a molded catalyst using only the synthetic lamellar magnesium silicate compound, the amount of sodium ion in the synthetic faujasite-type zeolite tends to be larger, and therefore the catalyst life is short in many cases.

The lamellar aluminum silicate compound of the present invention is a compound having a lamellar crystalline structure composed of at least a silicon element, an aluminum element and an oxygen element. Examples of the compound include a natural clay compound mainly composed of at least one substance selected from montmorillonite, beidellite and kaolinite and a purified product thereof. Among them, a purified bentonite, which is a clay compound mainly composed of montmorillonite, is particularly preferred. Specific examples of the above-described purified bentonite include Bengel, Bengel HV, Bengel HVP, Bengel FW, Bengel Bright 11, Bengel Bright 23, Bengel Bright 25, and Bengel A manufactured by Nihon Yuukinendo Co., Ltd. The type of the interlayer cation of the lamellar aluminum silicate compound of the present invention is not particularly limited, but the sodium ion type or mixed type of sodium ion and calcium ion is particularly preferred.

Meanwhile, the synthetic lamellar magnesium silicate compound of the present invention is a compound having a lamellar crystalline structure composed of at least a silicon element, a magnesium element and an oxygen element, and refers to a chemically synthesized product and a product obtained by modifying a natural clay compound. Examples of the compound include a synthetic hectorite and a synthetic mica, which are chemically synthesized from a salt of sodium, lithium or magnesium and sodium silicate, and a modified hectorite and a modified mica, which are obtained by modifying a natural clay compound. Among them, a synthetic hectorite obtained by chemical synthesis is particularly preferred. Specific examples of the above-described synthetic hectorite include Laponite RD, Laponite RDS and Laponite OG manufactured by Rockwood Additives, and Lucentite SWN and Lucentite SWF manufactured by Co-op Chemical Co., Ltd.

The synthetic hectorite is a trioctahedral-type lamellar silicate having a smectite structure, and various synthetic methods thereof are known. The method for chemically synthesizing a synthetic hectorite which can be used in the present invention is not particularly limited, and it is possible to use publicly-known methods, for example, the method for producing a synthetic swellable silicate described in Japanese Laid-Open Patent Publication No. H06-345419, the method for producing a hectorite-like silicate described in Japanese Laid-Open Patent Publication No. H09-249412, and the method for producing synthetic magnesium silicate described in Japanese Laid-Open Patent Publication No. H11-71108. The type of the interlayer cation of the synthetic lamellar magnesium silicate compound of the present invention is not particularly limited, but the sodium ion type is preferred.

The adsorption amount of sodium ion varies depending on the type of the lamellar aluminum silicate compound, and the release amount of sodium ion varies depending on the type of the synthetic lamellar magnesium silicate compound. Therefore, the optimum mixing ratio between the lamellar aluminum silicate compound and the synthetic lamellar magnesium silicate compound in the present invention varies depending on the combination of the lamellar aluminum silicate compound and the synthetic lamellar magnesium silicate compound to be used. Based on the weight ratio, the mixing ratio between the lamellar aluminum silicate compound and the synthetic lamellar magnesium silicate compound is preferably 1:5 to 6:1, more preferably 1:5 to 4:1, even more preferably 1:5 to 7:2, and most preferably 1:5 to 3:1.

When the ratio of the lamellar aluminum silicate compound is smaller than the above-described range, the catalyst life tends to be shortened. It is considered that this is because the amount of free sodium in the molded catalyst increases. When the ratio of the lamellar aluminum silicate compound is larger than the above-described range, the amount of by-produced DME tends to be larger. It is considered that this is because the amount of sodium ion in the synthetic faujasite-type zeolite in the molded catalyst after molding is smaller than the appropriate range, as described above.

The ratio of the total amount of the lamellar aluminum silicate compound and the synthetic lamellar magnesium silicate compound to the total amount of the synthetic faujasite-type zeolite, the lamellar aluminum silicate compound and the synthetic lamellar magnesium silicate compound in the molded catalyst of the present invention is preferably 3 to 30% by weight, and particularly preferably 5 to 20% by weight in consideration of ease of molding, mechanical strength of the molded body, etc.

Further, to the molded catalyst of the present invention, a molding aid and a lubricant can be added for improving moldability. For example, carboxymethyl cellulose, stearic acid, alcohols, surfactants, fibers, etc. can be used.

The method for molding the molded catalyst of the present invention is not particularly limited, and various methods including the extrusion molding method, tumbling granulation method and tablet molding method can be employed according to the shape of the molded body. Further, the shape of the molded body is not particularly limited, and for example, a spherical shape, a column shape, a ring shape, a petal shape, etc. can be employed.

The pH value of an aqueous dispersion obtained by dispersing the molded catalyst of the present invention in water at a ratio of 2% by weight is preferably 10.2 to 10.8. When the pH value of the aqueous dispersion is lower than 10.2, the amount of by-produced DME tends to be larger. It is considered that this is because the amount of sodium ion in the synthetic faujasite-type zeolite in the molded catalyst after molding is smaller than the appropriate range. When the pH value of the aqueous dispersion is higher than 10.8, the amount of by-produced DME can be reduced, but the catalyst life tends to be shortened.

The amount of free sodium in the molded catalyst of the present invention is preferably 0.03 milliequivalent/g or less. When the amount of free sodium in the molded catalyst is larger than the above-described value, the amount of byproduced DME is smaller, but the catalyst life tends to be shortened.

Hereinafter, the method for producing methyl methacrylate of the present invention will be described. The method for producing methyl α-hydroxyisobutyrate as a raw material is not particularly limited, and it is possible to use methyl α-hydroxyisobutyrate produced by methanolysis of α-hydroxyisobutyric acid amide or amide-ester exchange of α-hydroxyisobutyric acid amide and methyl formate disclosed in Japanese Publication for Opposition No. H02-2874. Further, methyl α-hydroxyisobutyrate can also be obtained from a high boiling point byproduct obtained by the ACH method, in which methyl methacrylate is produced from acetone cyanhydrin and sulfuric acid, or the C4 oxidation method using isobutylene as a raw material. Methyl α-hydroxyisobutyrate recovered from such a high boiling point byproduct generally contains methyl α- or β-methoxyisobutyrate. The catalyst of the present invention is also effective for demethanolation reaction of such homologues, and these can be recovered as methyl methacrylate.

The reaction of the present invention can be performed in the fixed bed gas-phase flow system, and a reactor of the heat insulation type, multi-tube heat exchange type or the like can be used. Methyl α-hydroxyisobutyrate as a raw material is preheated and vaporized, and then supplied to the reactor. The vaporized raw material can be directly introduced or introduced after diluted with an inert gas such as nitrogen, argon and helium. In order to improve the yield of methyl methacrylate, it is more preferred to use methanol as a diluent. The ratio of methanol as the diluent is preferably 0.1 to 3.0 times by weight, and particularly preferably 0.2 to 2.0 times by weight of methyl α-hydroxyisobutyrate. Regarding the feeding rate of the raw material, the total weight of methyl α-hydroxyisobutyrate as the raw material and methanol as the diluent per unit catalyst weight, i.e., the weight hourly space velocity (WHSV) is preferably 0.1 to 5.0 $hr^{-1}$.

The reaction temperature is preferably 230 to 300° C. and may be held at a constant temperature. However, in order to suppress various byproducts and maintain the catalytic activity, it is more preferred to employ a method of slowly increasing the temperature within a specific temperature range over the reaction time so that the reaction rate of methyl α-hydroxyisobutyrate is maintained within the range of 98.0 to 99.9%. In this case, the reaction initiation temperature is 230 to 270° C., and more preferably 240 to 260° C., and the reaction completion temperature is 250 to 300° C., and more preferably 260 to 290° C. The adjustment of the reaction temperature in this way is required for covering time-dependent decrease of active sites due to attachment of a high boiling point byproduct, etc. to the catalyst. When it is no longer possible to maintain the reaction rate of methyl α-hydroxyisobutyrate within the range of 98.0 to 99.9% within the aforementioned reaction temperature range, the raw material feeding is temporarily stopped, and calcining in air is carried out at a temperature at which the FAU-type structure of the catalyst is not destroyed, preferably not higher than 550° C., thereby recovering the catalytic activity almost completely. Thus, the catalyst of the present invention can be easily recovered and used repeatedly. The reaction pressure is not particularly limited, but the reaction can be performed under ordinary pressure or slightly elevated pressure.

The reaction product solution obtained by the method of the present invention contains unreacted raw materials and byproducts such as methacrylic acid, acetone and polymethylbenzenes in addition to methyl methacrylate as the objective substance. Such byproducts can be easily separated by applying thereto a usual purification method such as distillation and extraction.

EXAMPLES

Hereinafter, the present invention will be specifically described by way of examples, but the present invention is not limited thereto. The performance test of methyl methacrylate synthesis reaction in the examples and comparative examples of the present invention was carried out as described below.

<Analysis of Molded Catalyst>
<Analysis of pH of Molded Catalyst>

The pH of the molded catalyst was analyzed as described below. A powdered molded catalyst component obtained by crushing the molded catalyst by agate or the like was mixed with water to prepare a mixture containing the molded catalyst component at a ratio of 2% by weight. After that, the mixture was subjected to the ultrasonic dispersion treatment and further left overnight to obtain a completely-dispersed aqueous dispersion. The pH of the aqueous dispersion was measured using a pH meter D-54 manufactured by HORIBA, Ltd.

<Analysis of Electrical Conductivity>

The electrical conductivity of the molded catalyst was analyzed as described below. A powdered molded catalyst component obtained by crushing the molded catalyst by agate or the like was mixed with water to prepare a mixture containing the molded catalyst component at a ratio of 2% by weight. After that, the mixture was subjected to the ultrasonic dispersion treatment and further left overnight to obtain a completely-dispersed aqueous dispersion. The electrical conductivity of the aqueous dispersion was measured using a pH meter D-54 manufactured by HORIBA, Ltd.

<Amount of Free Sodium (Amount of Free Na)>

4 wt % aqueous dispersion of the molded catalyst was prepared, and then it was left overnight. A supernatant thereof was titrated with 0.01N hydrochloric acid to obtain the amount of free Na in the molded catalyst from a calculated value.

<Performance Test of Methyl Methacrylate Synthesis Reaction>

The performance test of the methyl methacrylate synthesis reaction was carried out using a fixed bed gas phase flow-type reaction apparatus equipped with a raw material tank, a raw material feeding pump, a raw material gas introduction apparatus, a reaction tube (made of SUS316, inner diameter: 18 mmφ, length: 300 mm), a cooling apparatus, a reaction product solution collection apparatus, etc. In the performance test, 7 g of a molded body subjected to particle size regulation to have a size of 10 to 20 mesh was put in the center of the reaction tube, a methanol solution containing 55 wt % of methyl α-hydroxyisobutyrate was supplied at 9 g/hr, and it was carried out under atmospheric pressure. The reaction temperature was gradually increased so that the reaction rate of methyl α-hydroxyisobutyrate was within the range of 99.5 to 99.9%, and the number of days until the reaction temperature reached 280° C. was regarded as the catalyst life. Reaction results were obtained by introducing the reaction product solution into a gas chromatograph to carry out quantitative analysis.

In this regard, the methanol recovery rate (MeOH recovery rate), the dimethyl ether yield (DME yield) and the total yield of methyl methacrylate and methacrylic acid (MMA+MAA yield) were calculated as follows:

(1) MeOH recovery rate (%)=(mole number of methanol in reaction product solution)/(mole number of methanol in raw material)×100

(2) DME production rate (%)=(mole number of dimethyl ether in reaction product solution×2)/(mole number of methanol in raw material)×100

(3) MMA+MAA yield (%)=(mole number of methyl methacrylate in reaction product solution+mole number of methacrylic acid in reaction product solution)/(mole number of methyl α-hydroxyisobutyrate in raw material)×100

Example 1

75.9 g of NaOH was dissolved in 462.9 g of ion-exchange water, and 27.7 g of sodium aluminate ($Al_2O_3$:51.0 wt %, $Na_2O$:36.0 wt %) was added thereto to be dissolved therein. In addition, a mixed solution of 333.0 g of silica sol ($SiO_2$:20 wt %) and 200.0 g of ion-exchange water was added thereto, and it was stirred until it became a homogeneous slurry mixture. The above-described mixture was put into an autoclave to perform crystallization at 100° C. for 48 hours. After that, the temperature was lowered to room temperature, and it was filtered, washed with water until the amount of free alkali in the filtrate became 0.01 milliequivalent/g, and then dried at 150° C., thereby obtaining 51.6 g of white zeolite powder. When this zeolite was subjected to X-ray diffraction and chemical composition analysis, it was synthetic faujasite-type zeolite with a lattice constant of 24.86 Å and Na/Al=0.96.

34 g of the above-described synthetic faujasite-type zeolite powder was mixed with 1.2 g of Bengel Bright 11 (purified bentonite manufactured by Nihon Yuukinendo Co., Ltd., the type of the interlayer cation is Ca and Na), which is a lamellar aluminum silicate compound in which the content of montmorillonite is 75 to 95%, and 4.8 g of Laponite RD (lot number: 10-4550, Laponite is a registered trademark), which is a synthetic hectorite commercially available from Rockwood Additives. Further, ion-exchange water was gradually added thereto while kneading well, and after that, the mixture was molded, dried at 150° C. and baked at 350° C., thereby obtaining a molded catalyst. The mixing ratio of the synthetic faujasite-type zeolite/Bengel Bright 11 (lamellar aluminum silicate compound)/Laponite RD (synthetic lamellar magnesium silicate compound) in the molded catalyst was 85/3/12 based on the weight ratio. The results of analysis of the molded catalyst are shown in Table 1, and the results of the performance test of the methyl methacrylate synthesis reaction are shown in Table 2. pH was 10.55, the electrical conductivity was 217 μS/cm, and the amount of free Na was 0.023 milliequivalent/g. When the aforementioned performance test of the methyl methacrylate synthesis reaction was carried out using the obtained molded catalyst, the catalyst life was 61 days, the MeOH recovery rate was 94.4%, the DME production rate was 4.0%, and the MMA+MAA yield was 93.3%. Each of these reaction results is the average value during the reaction.

Example 2

A catalyst was prepared in a manner similar to that in Example 1, except that Bengel (purified bentonite manufactured by Nihon Yuukinendo Co., Ltd., the type of the interlayer cation is Na), in which the content of montmorillonite is 85 to 99%, was used instead of Bengel Bright 11 and the mixing ratio of the synthetic faujasite-type zeolite/Bengel (lamellar aluminum silicate compound)/Laponite RD (synthetic lamellar magnesium silicate compound) was set to be 90/7/3 based on the weight ratio. The performance test of the methyl methacrylate synthesis reaction was carried out using the obtained molded catalyst. The results of analysis of the molded catalyst are shown in Table 1, and the results of the performance test of the methyl methacrylate synthesis reaction are shown in Table 2.

Comparative Example 1

A catalyst was prepared in a manner similar to that in Example 1, except that the mixing ratio of the synthetic faujasite-type zeolite/Bengel Bright 11 (lamellar aluminum silicate compound)/Laponite RD (synthetic lamellar magnesium silicate compound) was set to be 85/15/0 based on the weight ratio and Laponite RD as a binder was not used. The performance test of the methyl methacrylate synthesis reaction was carried out using the obtained molded catalyst. The results of analysis of the molded catalyst are shown in Table 1, and the results of the performance test of the methyl methacrylate synthesis reaction are shown in Table 2.

Comparative Example 2

A catalyst was prepared in a manner similar to that in Example 1, except that the mixing ratio of the synthetic faujasite-type zeolite/Bengel Bright 11 (lamellar aluminum silicate compound)/Laponite RD (synthetic lamellar magnesium silicate compound) was set to be 85/0/15 based on the weight ratio and Bengel Bright 11 as a binder was not used. The performance test of the methyl methacrylate synthesis reaction was carried out using the obtained molded catalyst. The results of analysis of the molded catalyst are shown in Table 1, and the results of the performance test of the methyl methacrylate synthesis reaction are shown in Table 2.

TABLE 1

| | Composition ratio of molded catalyst (wt %) | | | | | |
| --- | --- | --- | --- | --- | --- | --- |
| | Synthetic faujasite-type zeolite | Lamellar aluminum silicate compound | Synthetic lamellar magnesium silicate compound | pH | Electrical conductivity μS/cm | Amount of free Na milliequivalent/g |
| Example 1 | 85 | 3 | 12 | 10.55 | 217 | 0.0228 |
| Example 2 | 90 | 7 | 3 | 10.23 | 146 | 0.0207 |
| Comparative Example 1 | 85 | 15 | 0 | 9.96 | 145 | 0.0207 |
| Comparative Example 2 | 85 | 0 | 15 | 10.83 | 233 | 0.0379 |

TABLE 2

|  | Catalyst life (day) | MeOH recovery rate (%) | DME production rate (%) | MMA + MAA yield (%) |
|---|---|---|---|---|
| Example 1 | 61 | 94.4 | 4.0 | 93.3 |
| Example 2 | 58 | 94.2 | 4.6 | 93.0 |
| Comparative Example 1 | 56 | 92.7 | 5.4 | 92.1 |
| Comparative Example 2 | 42 | 93.5 | 4.1 | 92.6 |

According to these Examples and Comparative Examples, it is understood that the molded catalysts of the Examples obtained by using a mixture of the lamellar aluminum silicate compound and the synthetic lamellar magnesium silicate compound as a binder in addition to the synthetic faujasite-type zeolite are excellent in the catalyst life and the methanol recovery rate compared to the catalysts of the Comparative Examples.

The invention claimed is:

1. A molded catalyst for use in the production of methyl methacrylate, for producing methyl methacrylate from methyl α-hydroxyisobutyrate as a raw material by means of a vapor phase contact reaction, wherein the molded catalyst comprises a synthetic faujasite-type zeolite, a lamellar aluminum silicate compound and a synthetic lamellar magnesium silicate compound, a weight ratio between the lamellar aluminum silicate compound and the synthetic lamellar magnesium silicate compound being 1:5 to 6:1.

2. An aqueous dispersion comprising the molded catalyst for use in the production of methyl methacrylate according to claim 1, wherein when an aqueous dispersion contains 2% by weight of the molded catalyst, the pH of the aqueous dispersion is 10.2 to 10.8.

3. The molded catalyst for use in the production of methyl methacrylate according to claim 1, wherein an amount of free sodium in the molded catalyst is 0.03 milliequivalent/g or less.

4. The molded catalyst for use in the production of methyl methacrylate according to claim 1, wherein the lamellar aluminum silicate compound and the synthetic lamellar magnesium silicate compound are 3 to 30% by weight of the synthetic faujasite-type zeolite, the lamellar aluminum silicate compound, and the synthetic lamellar magnesium silicate compound.

5. The molded catalyst for use in the production of methyl methacrylate according to claim 1, wherein the lamellar aluminum silicate compound is a clay compound mainly composed of at least one substance selected from montmorillonite, beidellite and kaolinite.

6. The molded catalyst for use in the production of methyl methacrylate according to claim 1, wherein the lamellar aluminum silicate compound is a clay compound mainly composed of montmorillonite.

7. The molded catalyst for use in the production of methyl methacrylate according to claim 1, wherein the synthetic lamellar magnesium silicate compound is a synthetic hectorite.

8. A method for producing methyl methacrylate, which comprises producing methyl methacrylate by means of a vapor phase contact reaction using methyl α-hydroxyisobutyrate as a raw material in the presence of the molded catalyst for use in the production of methyl methacrylate according to claim 1.

9. The method for producing methyl methacrylate according to claim 8, wherein methanol is used as a diluent in an amount of 0.1 to 3.0 times by weight of methyl α-hydroxyisobutyrate.

* * * * *